United States Patent [19]
Hluchy et al.

[11] Patent Number: 5,688,222
[45] Date of Patent: Nov. 18, 1997

[54] ENDOSCOPIC INSTRUMENT

[75] Inventors: Heinz Hluchy, Hamburg; Thomas Prescher, Halstenbek, both of Germany

[73] Assignee: Olympus Winter & Ibe GmbH, Hamburg, Germany

[21] Appl. No.: 654,247

[22] Filed: May 28, 1996

[30] Foreign Application Priority Data

Jun. 2, 1995 [DE] Germany ............... 195 20277.5

[51] Int. Cl.$^6$ ............................................. A61B 1/12
[52] U.S. Cl. ...................... 600/156; 600/157; 600/135
[58] Field of Search ............................. 600/153, 155, 600/156, 157, 158, 105, 135, 137, 138

[56] References Cited

U.S. PATENT DOCUMENTS

| | | | |
|---|---|---|---|
| 3,939,839 | 2/1976 | Curtiss | 600/105 X |
| 4,770,163 | 9/1988 | Ono et al. | 600/156 X |
| 5,509,892 | 4/1996 | Bonnet | 600/157 X |

*Primary Examiner*—Beverly M. Flanagan
*Attorney, Agent, or Firm*—Walter C. Farley

[57] ABSTRACT

An endoscopic instrument with an inner sheath carrying instrument optics and an outer sheath enclosing the inner sheath so as to form a gap between the sheaths, the outer sheath having apertures radially through its distal end zone to provide fluid communication between the gap and the surroundings of the outer sheath. The inner sheath acts as a supply duct and the gap between the inner and outer sheaths acts as an evacuation duct for the rinsing fluid. A hole connects the interior of the inner sheath to the gap at the distal end of the inner sheath, the clear cross-section of the hole being substantially less than the sum of the cross-sections of the apertures at the distal zone of the outer sheath.

3 Claims, 1 Drawing Sheet

ENDOSCOPIC INSTRUMENT

FIELD OF THE INVENTION

This invention relates to an endoscopic instrument having optics housed in an inner sheath and an outer sheath spaced from the inner sheath to form a flushing channel.

BACKGROUND OF THE INVENTION

Instruments of this general type are typically used in transurethral or transcervical interventions, particularly in resections. The instruments comprise an inner sheath housing the optics and sometimes also a support for a resecting loop which cuts in the axial direction. The remaining free lumen of the inner sheath is configured as a supply duct for rinsing fluid. During the intervention, rinsing or flushing fluid is constantly moved through the supply duct over the distal end of the optics to rinse clear the operated zone and to ensure a clear view.

Instruments of this type also have an outer sheath enclosing the inner one and spaced therefrom to form a gap relative to the inner sheath. The gap is in fluid communication through distal apertures in the outer sheath with the surroundings of the instrument and is used as an evacuation duct for the introduced rinsing fluid.

During continuous rinsing, the rinsing fluid issues from the distal end of the inner sheath into the bladder, for example, and from there it is evacuated through the apertures in the distal zone of the outer sheath into the gap between the outer and inner sheaths and then is evacuated again.

A problem arises in that the entire length of an endoscopic instrument of this type may, under certain conditions of intervention, be positioned, for example, in the cervical canal or urethra. Illustratively, this will be the case when intervention is carried out directly at the bladder entry. In such a case, the distal apertures in the outer sheath are covered by the surrounding canal-wall tissue and the rinsing fluid no longer can be evacuated. In order to assure the desired constant bladder or uterus inside pressure during the intervention, the otherwise continuous rinsing must be interrupted in such situations when using conventional instruments, in other words, rinsing must be curtailed drastically. As a result insufficient or no rinsing at all takes place at the distal optics end, and a clear view of the operational zone is degraded.

SUMMARY OF THE INVENTION

Therefore, in the light of the state of the art, an object of the present invention to provide an endoscopic instrument allowing continuous rinsing of the distal end of the endoscope optics even when conditions tending to block fluid flow passages arise.

Briefly described, the invention includes an endoscopic instrument with an inner sheath containing instrument optics, an outer sheath enclosing the inner sheath, and means separating an outer wall of said inner sheath from an inner wall of said outer sheath to form a gap therebetween. Apertures through a distal end zone of the outer sheath provide fluid communication between surroundings of the outer sheath and the gap. Rinsing fluid is pumped into the inner sheath so that the inner sheath acts as a supply duct and the gap between the inner and outer sheaths acts as a rinsing fluid evacuation duct. At least one hole (20) through a distal end zone of the inner sheath provides communication between the inner sheath and the gap, the hole having a clear diameter substantially less than the sum of cross-sections of the apertures through the distal zone of the outer sheath.

Because of the at least one hole at the distal end zone of the inner sheath, the gap between inner and outer sheaths is connected with the supply duct formed in the inner sheath. Rinsing fluid from the supply duct can directly flow through this hole into the evacuation duct. Accordingly, the instruments of the invention are able to operate in a continuous rinsing mode, even when the apertures in the outer sheath are partly or entirely closed, such as when in the cervical canal or in the urethra. The rinsing fluid flows directly from the supply duct through the hole into the evacuation duct and no longer issues, or only slightly, from the instrument.

Satisfactory rinsing of the field of view is also achieved if the distal optics end to be rinsed is designed to be located behind the hole of the invention in the inner sheath as seen in the distal direction. Surprisingly, it was found that in this case also, a flow of rinsing fluid passing through the inner hole reaches at least in part the distal optics end and is able to clear the field of view.

Basically, the bypass hole of the invention is intended to preserve the rinsing features of the endoscopic instrument only when the primarily desired continuous rinsing through the apertures in the outer sheath is impossible because of blockage. If, however, the apertures in the outer sheath are free, then the rinsing fluid also exits the distal end of the inner sheath of the instrument of the invention and, in the manner of instruments of this general type, flows back through the apertures in the outer sheath into the evacuation duct. To ensure this feature, the cross-section of the hole of the invention must be made significantly smaller than the sum of the cross-sections of the apertures in the outer sheath. Only in this manner is it possible for the rinsing fluid to reliably issue in normal operation from the inner sheath at the distal end rather than prematurely through the hole of the invention. The particular matching of the hole cross-section to the summed cross-sections of the apertures in the outer sheath can be carried out in a simple manner by the expert in relation to the particular rinsing conditions and the desired properties by preliminary tests.

In a further embodiment, the distal end of the outer sheath is formed with an arcuate space which at least partly surrounds or encloses the inner sheath. This arcuate space communicates with the gap between the inner and outer sheaths that is acting as the evacuation duct. In case of blockage, that is when the other apertures through the outer sheath are covered, rinsing fluid issuing from the inner sheath is able to flow back through the arcuate space into the evacuation duct. In this solution also, continuous rinsing can be preserved in critical situations.

In another embodiment, the arcuate space is interrupted by inward projections from the outer sheath to the outer wall of the inner sheath. Advantageously, these projections act as guide rests for the outer sheath on the inner one: almost always conventional instruments are designed so that the inner and outer sheaths are mutually rotatable. In this case the projections constitute a distal guide rest for the outer sheath on the inner one.

BRIEF DESCRIPTION OF THE DRAWINGS

Preferred embodiments of the invention are described below with reference to the accompanying drawings wherein.

DESCRIPTION OF THE PREFERRED EMBODIMENTS

Figure 1:
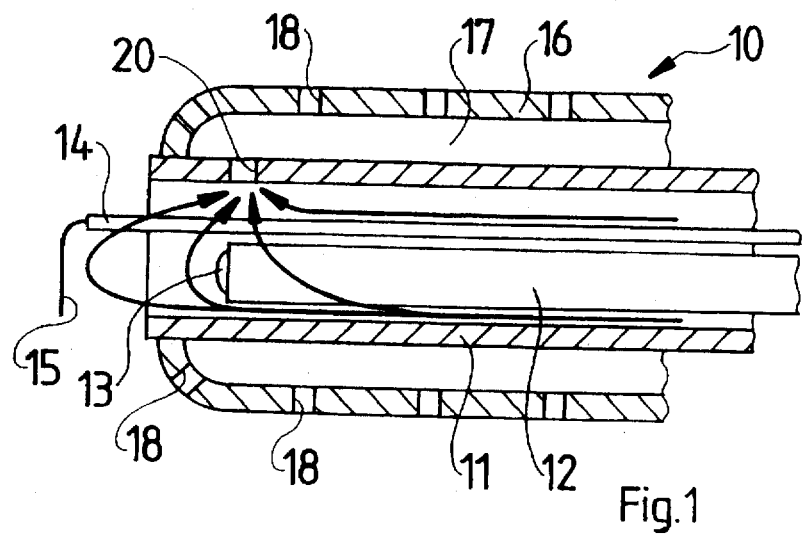
FIG. 1 is a partial side elevation of the distal end of an instrument in accordance with the invention with a hole in the inner sheath.

FIG. 1 shows the distal end region of an endoscopic instrument indicated generally at 10. Instrument 10 comprises an inner sheath 11 housing endoscope optics 12 with an objective 13 at its distal end. Inner sheath 11 also houses a support 14 for an axially actuated resection loop 15. Inner sheath 11 is enclosed by an outer sheath 16 and a gap 17 is established and maintained between the two sheaths. The distal end of outer sheath 16 bends inwardly to form means for maintaining the gap between the sheaths.

Instrument 10 of the invention is to be operated with continuous rinsing during intervention for a medical procedure, just as are the conventional instruments in this respect. For that purpose, inner sheath 11 is used as a rinsing fluid supply duct. In normal operation, the fluid passes through inner sheath 11 and issues from its distal end into the operational zone from which it flows back through the apertures 18 present in the outer sheath 16 into the gap between the outer and inner sheaths 16 and 11. Annular gap 17 thus acts as an evacuation duct for the rinsing fluid.

In some positions of intervention, as described above, apertures 18 in the outer sheath 16 may become blocked by the surrounding tissue. This is the case, for instance, when endoscopic instrument 10 is used for intervention at the bladder entry. In such circumstances the instrument is received over most of its length in the urethra which then also encloses the apertures in the distal end of the instrument 10. When this is the case, the rinsing fluid supplied through the inner sheath for instance to the bladder no longer can be evacuated through openings 18. The flow of rinsing fluid then either stops by itself because of the increased bladder pressure or it is suppressed by an appropriate control.

In accordance with the invention, instrument 10 has an additional hole 20 through the distal end of inner sheath 11 to directly connect the inner sheath to gap 17. When normal continuous rinsing through the apertures 18 is no longer assured, the rinsing fluid in instrument 10 of the invention is able to pass directly from inner sheath 11 through hole 20 into gap 17 acting as the evacuation duct. Depending on design, hole 20 may be located proximally of objective 13, as seen in the distal direction, and as also shown in FIG. 1. Surprisingly, it was found that even in this case the rinsing fluid evacuated through hole 20 reaches the zone in front of (i.e., distally of) objective 13 and flushes it clear. It is believed that only a portion of the rinsing fluid flowing from inner sheath 11 passes on its shortest path through hole 20. Another portion of the rinsing fluid initially flows distally of hole 20 and then bends back toward it. These flow paths are indicated schematically by several arrows in FIG. 1, the left arrow indicating that portion of the rinsing fluid which reaches the zone between resection loop 15 and objective 13 and cleaning that zone.

As already mentioned, the instrument of the invention also is designed so that in normal operation, the rinsing fluid emerges from the end of inner sheath 11 into the operational zone and is evacuated through apertures 18 and gap 17. The instrument of the invention is, however, intended also to provide adequate rinsing in front of the objective 13 in those situations wherein apertures 18 are all or partly covered. Accordingly, hole 20 must be sized in such a way that in normal operation only a slight portion of the rinsing fluid is evacuated through hole 20 while the remainder issues in the desired manner from the distal optics end into the operational zone. Appropriately, the cross-sectional area of hole 20 must be substantially less than the sum of the cross-sectional areas of apertures 18. The precise sizing and matching of the hole 20 can be decided by the expert in relation to the special applications. Rigorous conditions cannot be laid down because of the large number of variables. Rather, depending on where the instrument will be used, on the configuration of the outer sheath, the quantity or rate of rinsing fluid and the pressure of this fluid, a large number of variations are conceivable which all are included within the invention. It is also possible for several holes to be provided to connect the inner sheath with the gap between the inner and outer sheaths.

Figure 2:
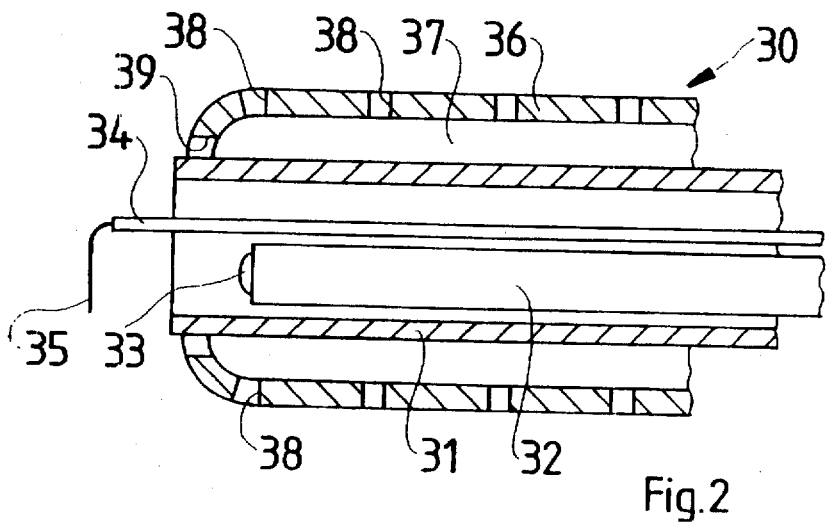
FIG. 2 is a view similar to FIG. 1 of a further embodiment of an instrument in accordance with the invention with an annular gap between the outer and inner sheaths.

FIG. 2 shows a further variation of an endoscopic instrument in accordance with the invention. This instrument 30 also comprises an inner sheath 31 housing an optics 32 with objective 33 at its distal end. A support 34 for an axially displaceable resection loop 35 is inside inner sheath 31. Inner sheath 31 is enclosed by an outer sheath 36 which is spaced from the inner sheath by a gap 37. Apertures 38 pass through the distal end zone of outer sheath 36 allowing the evacuation of rinsing fluid supplied through the inner sheath into the operational zone. In the event that apertures 38 are covered, this embodiment provides that the inwardly bent distal end of outer sheath 36 is interrupted to form arcuate spaces 39 surrounding the distal end of sheath 31. Arcuate spaces 39 allow rinsing fluid issuing from the inner sheath to be evacuated in case apertures 38 are covered. Arcuate space 39 has a cross-sectional area substantially less than the sum of cross-sectional areas of apertures 38 through the distal zone of the outer sheath. This variation also assures in all circumstances that the operational zone in front of the objective 33 can uninterruptedly be rinsed during problematical interventions (wherein the apertures 38 are covered) and that clear viewing is assured.

Figure 3:
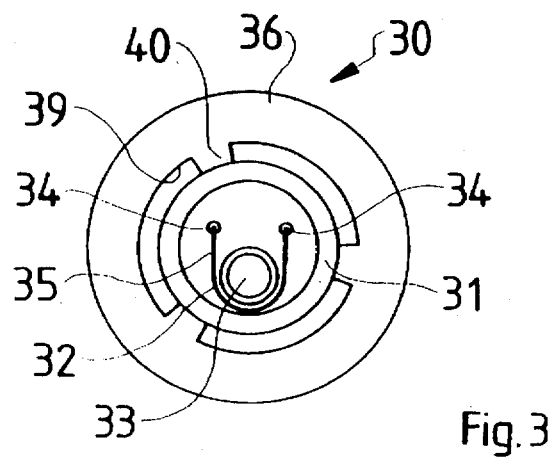
FIG. 3 is a distal end elevation of the instrument of FIG. 2.

FIG. 3 is an end elevation of the distal end of instrument 30 shown in FIG. 2. It shows the outer sheath 36 enclosing inner sheath 31 and optics 32 with objective 33 and support 34 with cutting loop 35 all housed in the inner sheath. Also shown are arcuate spaces 39 formed between the distal end of the outer sheath 36 and the inner sheath 31. Arcuate spaces 39 are interrupted by radial projections 40 remaining from the inwardly bent end of the outer sheath, extending inwardly from the inner surface of sheath 36 as far as the outer surface of inner sheath 31. Almost always in such instruments, the outer and inner sheaths 36 and 31 are designed to be mutually rotatable. In this embodiment, projections 40 act as guides and rests for the outer sheath 36 on the inner sheath 31, the inner ends of the projections being slidable on the outer surface of the inner sheath as rotation occurs.

The two embodiments in accordance with the invention shown in FIGS. 1, 2 and 3 assure in a manner unknown heretofore that instruments of the this type can always rinse clear the zone in front of the objective of the endoscope optics-no matter what the particular intervention may be.

What is claimed is:

1. An endoscopic instrument comprising
   an inner sheath containing instrument optics;
   an outer sheath enclosing said inner sheath;
   means separating an outer wall of said inner sheath and an inner wall of said outer sheath to form a gap therebetween;
   a plurality of apertures (18) through a distal end zone of said outer sheath to provide fluid communication between surroundings of said outer sheath and said gap;

means for supplying rinsing fluid into said inner sheath so that said inner sheath acts as a supply duct and said gap between said inner and outer sheaths acts as a rinsing fluid evacuation duct; and at least one hole (20) through a distal end zone of said inner sheath (11) to provide communication between said inner sheath (11) and said gap (17), said hole (20) having a cross-sectional area substantially less than the sum of cross-sectional areas of said apertures (18) through said distal zone of said outer sheath (16).

2. An endoscopic instrument comprising an inner sheath containing instrument optics;

an outer sheath enclosing said inner sheath;

means separating an outer wall of said inner sheath and an inner wall of said outer sheath to form a gap therebetween;

a plurality of apertures (38) through a distal end zone of said outer sheath to provide fluid communication between surroundings of said outer sheath and said gap;

means for supplying rinsing fluid into said inner sheath so that said inner sheath acts as a supply duct and said gap between said inner and outer sheaths acts as a rinsing fluid evacuation duct; and an arcuate space (39) through a distal end zone of said outer sheath (36) at least partly enclosing said inner sheath (31) to provide communication between said surroundings of the distal end of said outer sheath and said gap (37) when said apertures (38) are at least partly blocked, said arcuate space having a cross-sectional area substantially less than the sum of cross-sectional areas of said apertures (38) through said distal zone of said outer sheath (36).

3. An endoscopic instrument according to claim 2 wherein said outer sheath comprises a plurality of radial projections (40) extending inwardly across said arcuate space (39) to said outer wall of said inner sheath (31).

* * * * *